United States Patent [19]

Swanson et al.

[11] Patent Number: 4,484,921
[45] Date of Patent: Nov. 27, 1984

[54] THEOPHYLLINE THERAPY UTILIZING OSMOTIC DELIVERY

[75] Inventors: David Swanson, Palo Alto; David Edgren, El Granada, both of Calif.

[73] Assignee: ALZA Corporation, Palo Alto, Calif.

[21] Appl. No.: 568,546

[22] Filed: Jan. 5, 1984

Related U.S. Application Data

[63] Continuation of Ser. No. 344,785, Feb. 1, 1982, , which is a continuation of Ser. No. 196,219, Oct. 14, 1980, Pat. No. 4,326,525.

[51] Int. Cl.³ ............................................. A61M 7/00
[52] U.S. Cl. ...................................... 604/892; 424/19
[58] Field of Search ............................... 604/890–897; 424/19–28

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,016,880 | 4/1977 | Theeuwes et al. | 128/260 |
| 4,077,407 | 3/1978 | Theeuwes et al. | 128/260 |
| 4,088,864 | 5/1978 | Theeuwes et al. | 219/121 |
| 4,160,020 | 2/1979 | Ayer et al. | 424/15 |
| 4,160,452 | 7/1979 | Theeuwes et al. | 604/893 |
| 4,326,525 | 4/1982 | Higuchi | 604/892 |

Primary Examiner—C. Fred Rosenbaum
Assistant Examiner—Harrie Stein Samaras
Attorney, Agent, or Firm—Paul L. Sabatine; Edward L. Mandell; Steven F. Stone

[57] ABSTRACT

An osmotic device is disclosed that provides a means for improving the delivery properties of a beneficial agent in situ.

4 Claims, 5 Drawing Figures

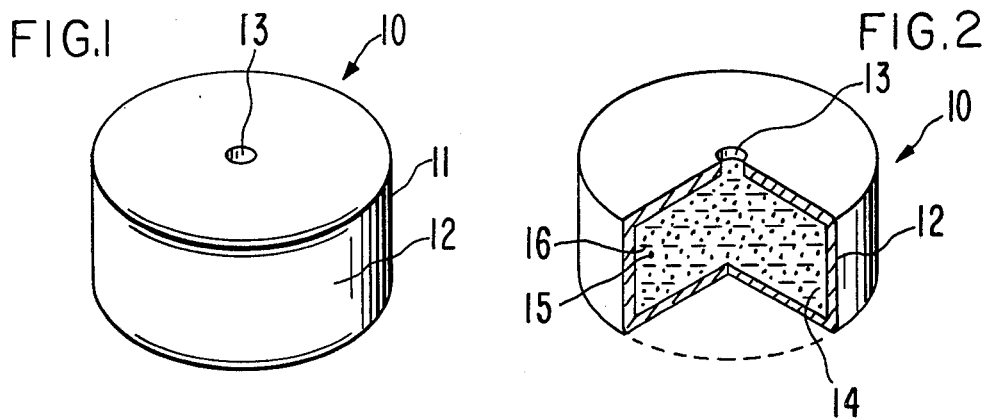
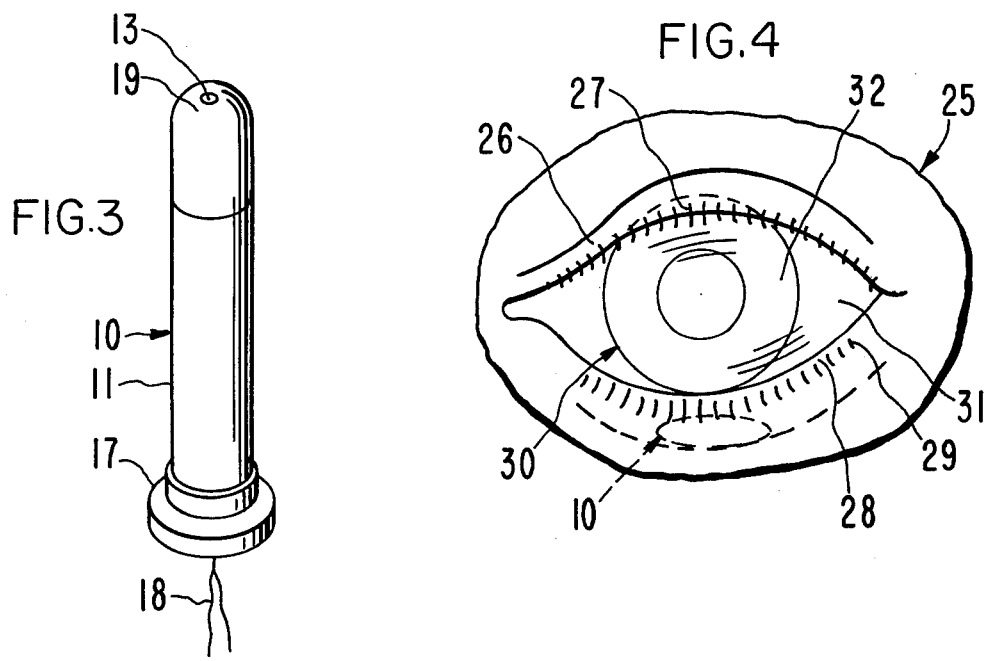
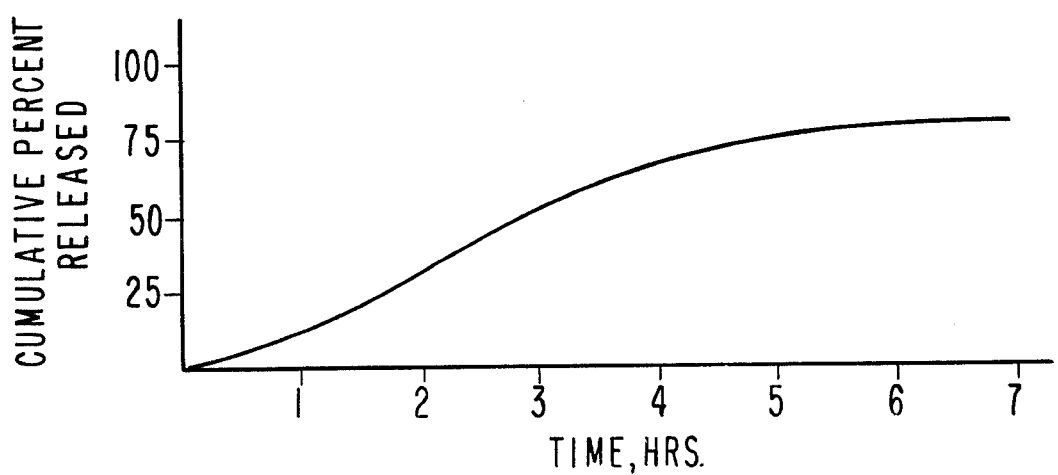

THEOPHYLLINE THERAPY UTILIZING OSMOTIC DELIVERY

CROSS-REFERENCE TO RELATED APPLICATIONS

This application is a continuation of application Ser. No. 06/344,785 filed Feb. 1, 1982, which application is a continuation of application Ser. No. 06/196,219 filed Oct. 14, 1980 and now U.S. Pat. No. 4,326,525 issued Apr. 27, 1982.

FIELD OF THE INVENTION

This invention pertains to an osmotic device. More particularly, the invention relates to an osmotic device comprising a semipermeable wall surrounding a compartment containing a beneficial agent and a buffer that react, when the device is in operation, to produce an agent with improved delivery properties. A passageway through the wall connects the exterior of the device with the compartment for delivering the improved agent from the device.

BACKGROUND OF THE INVENTION

Osmotic devices for delivering a beneficial agent to an environment of use are known to the prior art in U.S. Pat. No. 3,845,770 issued to Theeuwes and Higuchi, and in U.S. Pat. No. 3,916,899, issued to the same patentees. The osmotic devices disclosed in those patents comprise a semipermeable wall surrounding a compartment containing an agent. The wall is permeable to the passage of an external fluid, and it is substantially impermeable to the passage of agent. The devices have a passageway through the wall that connects the compartment with the exterior of the device for delivering the agent from the device. These devices deliver an agent by imbibing fluid through the wall into the compartment, at a rate determined by the permeability of the wall and the osmotic pressure gradient across the wall, to produce an aqueous solution containing agent that is delivered through the passageway from the device. The devices are effective for delivering an agent that is soluble in fluid imbibed into the compartment, thereby forming a solution of the agent that is delivered from the device, and also for delivering an agent that s poorly soluble in the fluid and is mixed with an osmotically effective solute that is soluble in fluid imbibed into the device, thereby forming a solution of the solute containing agent in suspension that is delivered from the device.

The prior art devices described above represent an outstanding and a pioneering advancement in the delivery art, and they are useful for delivering innumerable agents to many environments of use. It will be appreciated by those versed in the art, that the usefulness of the devices can be increased, and their application broadened, if a device and method are provided for improving the delivery characteristics of certain agents that are difficult to deliver from osmotic devices. For example, both the use and the value of a device would be unexpectedly increased, if (1) a device and a method are provided that during the operation of the device, the solubility of an agent that is poorly soluble in the fluid is enhanced, such that it no longer requires an added osmotically effective solute for its delivery as the agent now operates as its own osmotically effective solute for its delivery from the device, and (2) if the solubility of an agent that is too high in the fluid and delivered in excessive amounts in a short time is decreased in the fluid, such that the agent can now be delivered at a meaningful rate and over a prolonged period of time.

OBJECTS OF THE INVENTION

Accordingly, it is an immediate object of this invention, to provide an osmotic device and method for the controlled delivery of a beneficial agent, and which device and method represent an improvement and an advancement in the osmotic delivery art.

Another object of the invention is to provide an osmotic device and method that can deliver an agent that is poorly soluble in aqueous and biological environments by converting the agent to a more soluble form for improving its delivery from the osmotic device.

Another object of the invention is to provide an osmotic device and method that can deliver an agent that is too soluble in aqueous and biological environments at improved rates by converting the agent to a less soluble form for improving its delivery from the osmotic device.

Yet another object of the invention is to provide an osmotic device that can produce the salt of a beneficial agent in the device, and which agent salt acts as its own osmotically effective solute for its delivery from the device.

Yet still another object of the invention is to provide an osmotic device that produces the salt of a beneficial agent in the device, and which salt produces a solution with imbibed fluid, that on its delivery from the device to an animal is compatible with the tissues of the animal.

Still another object of the invention is to provide an osmotic device with a broadened application by making available a device that synthesizes an osmotically effective solute in the device for its delivery from the device.

Still another object of the invention is to provide a method for controlling the solubility of an agent in an osmotic device by providing an environment in the device comprising an agent and a buffer that can interact and produce an agent with a preselected solubility for its delivery from the device.

Other objects and advantages of the invention will be more apparent to those versed in the delivery art from the following detailed specification taken in conjunction with the drawings and the accompanying claims.

SUMMARY OF THE INVENTION

This invention concerns an improvement in osmotic devices. The device comprises a semipermeable wall surrounding a compartment connected with the exterior of the device through a passageway in the wall. The improvement comprises housing in the device an agent requiring a modification in its solubility, because of its poor or its high solubility in aqueous and biological fluids, and a buffer, which agent and buffer interact in the device to produce an agent with controlled solubility in the fluid. The improved, modified agent is dispensed through the passageway to the environment of use. The invention also concerns a method for regulating the solubiltiy of an agent in the device for improving its effective delivery from the device.

BRIEF DESCRIPTION OF THE DRAWINGS

In the drawings, which are not drawn to scale, but are set forth to illustrate various embodiments of the invention, the figures are as follows:

FIG. 1 is a view of an osmotic device designed for orally administering a beneficial agent to the gastrointestinal tract;

FIG. 2 is a view of the osmotic device of FIG. 1 seen in opened section for illustrating the internal structure of the device;

FIG. 3 depicts another osmotic device provided by the invention, which device is designed for delivering a beneficial agent to the ano-rectal and vaginal passageways; and, FIG. 4 is a front view of a human eye illustrating an osmotic device manufactured as an ocular insert in operative drug dispensing position in the eye; and, FIG. 5 is a graph depicting the cumulative percent released from a device over time.

In the drawings and the specification, like parts in related figures are identified by parts in related figures are identified by like numbers. The terms appearing earlier in the specification, and in the description of the drawings, as well as embodiments thereof, are further detailed elsewhere in the disclosure.

DETAILED DESCRIPTION OF THE DRAWINGS

Turning now to the drawings in detail, which are examples of various osmotic delivery devices provided by the invention, and which examples are not to be considered as limiting the invention, one example of an osmotic device is indicated in FIG. 1 by the numeral 10. In FIG. 1, device 10 comprises a body 11 having a wall 12 that surrounds a compartment 14, as seen in FIG. 2, and a passageway 13 in wall 12 that communicates with compartment 14 and the exterior of device 10.

In FIG. 2, device 10 of FIG. 1 is seen in opened-section with a portion of wall 12 removed for illustrating the internal structure of device 10. Device 10 comprises a wall 12 that surrounds and defines a compartment 14. A passageway 13 in wall 12 connects compartment 14 with the exterior of device 10 for delivering a beneficial agent from compartment 14 to the exterior of device 10. Wall 12 of device 10 comprises a semipermeable polymeric material that is permeable to the passage of an exterior fluid present in the environment of use, and wall 12 is substantially impermeable to the passage of agents and other compounds in compartment 14 or in the exterior environment. Wall 12 is substantially inert; it maintains its physical and chemical integrity during the dispensing of an active beneficial agent, and wall 12 when used for medical and veterinary applications is formed of a semipermeable material that is non-toxic to the host.

Compartment 14 houses a beneficial agent identified by dots 15, and a buffer identified by dashes 16. Agents, in a presently preferred embodiment, that can be delivered by device 10 include agents that need an improvement or modification in their physical and chemical properties and are difficult to deliver because of their solubility in an exterior fluid, which fluid includes aqueous and biological fluids. These agents in one embodiment are poorly soluble in the fluids and exhibit a solubility of less than 50 milligrams in one milliliter of solution, and in another embodiment the agents are highly soluble in the fluids and exhibit a solubility greater than 600 milligrams in one milliliter of solution. Agent 15, in either embodiment, is initially present in compartment 14 as a member selected from the group consisting essentially of the free acid or the free base of the agent. The buffer 16 in the compartment, is soluble in the exterior fluid and it exhibits an osmotic pressure gradient across wall 12 with the exterior fluid. Buffer 16 is initially present in compartment 14 as a member selected from the group consisting essentially of the counter acid or the counter base of the corresponding free base or the free acid of the agent. The amount of buffer in the compartment is preferably in excess of the total amount needed for all of agent 15 to react stoichiometrically with buffer 16 and produce an agent with the desired solubility. The compartment optionally contains the excess buffer for maintaining a buffered environment, such as neutral, acidic or basic, in the compartment throughout the prolonged period of time the agent is delivered from the device.

Device 10 of FIGS. 1 and 2 can be manufactured in many embodiments, including the presently preferred embodiment for oral use. Oral osmotic device 10 is used for delivering a locally or systemically acting therapeutic agent in the gastro-intestinal tract over time. Oral device 10 can embrace various conventional shapes and sizes such as round with a diameter of 3/16 inches to ½ inches, or it can be shaped like a capsule having a range of sizes from triple zero to zero and from 1 to 8. In these forms, device 10 can be adapted for administering therapeutic agents to animals, including warm-blooded mammals and humans, avians, reptiles and fishes.

FIG. 3 illustrates another embodiment of the invention designed for easy insertion and prolonged retention in a body passageway, such as a vagina or an ano-rectal canal. Device 10 of FIG. 3 has an elongated, cylindrical, self-sustaining shape with a rounded lead end 19, and a trailing end or base 17 equipped with a string 18 for easily removing device 10 from a body passageway, not shown. Device 10 is structurally identical with device 10 as described above and it operates in a like manner.

Referring to FIG. 4, an osmotic device 10, manufactured as an ocular insert, is seen in an eye 25 for administering an ocular drug at an osmotically metered dosage rate thereto. In FIG. 4, eye 25 comprises an upper eyelid 26 with eyelashes 27 and a lower eyelid 28 with eyelashes 29. Eye 25 is comprised of an eyeball 30 covered for the greater part by sclera 31 and at its center area by cornea 32. Eyelids 26 and 28 are lined with an epithelial membrane or palpebral conjunctiva, and sclera 31 is lined with a bulbar conjunctiva that covers the exposed surface of eyeball 30. Cornea 30 is covered with a transparent epithelial membrane. The portion of the palpebral conjunctiva which lines upper eyelid 26 and the underlying portion of the bulbar conjunctiva define an upper clu-de-sac, while that portion of the palpebral conjunctiva which lines lower eyelid 28 and the underlying portion of the bulbar conjunctiva define a lower cul-de-sac. Osmotic insert 10, seen in broken lines, is designed for placement in the upper or lower cul-de-sac. Insert 10 is seen in the lower cul-de-sac and it is held in place by the natural pressure of lower eyelid 28. Insert 10 contains an ophthalmic drug for release to eye 25 at a controlled rate and continuously over a prolonged period of time.

Ocular insert 10, as manufactured according to the principles described supra, can have any geometric shape that fits comfortably in the cul-de-sac. Typical shapes include ellipsoid, bean, banana, circular, ring, rectangular, doughnut, crescent, and half-ring shaped inserts. In cross-section the insert can be doubly convex, concavo-convex, retangular and the like, as the insert in use tends to conform to the shape of the eye. The dimensions of an ocular insert can vary widely with the lower limits governed by the amount of drug to be administered to the eye as well as the smallest sized insert that can be placed in the eye. The upper limits on the size of the insert is governed by the space limitations in the eye consistent with comfortable retention in the eye. Satisfactory insert can have a length of 4 to 20 millimeters, a width of 1 to 15 millimeters, and a thickness of 1 to 4 millimeters. The ocular inserts can contain from 0.15 micrograms to 275 milligrams of drug, or more for release over time.

The present invention, as exemplified in FIGS. 1 through 4 by device 10, comprising agent 15 and buffer 16 in compartment 14 contribute many important advantages for delivering agent 15 from osmotic device 10. For example, the preferred solubility of the agent can be made in situ instead of specially preparing the agent by a chemical process before it is placed in the device; a greater solubility range and osmotic driving force can be provided in the compartment through in situ pH adjustment; a means is provided for controlling the pH of a solution in situ, which aids in controlling the solubility of the agent in the device without previously isolating a particular form of the agent; a means is provided for using presently available forms of an agent concurrently with the buffer for in situ solubilization of the agent; the pH of a saturated solution of the agent can be selected to avert possible damage to the wall of the device and to the lining of the receiving tissues; and, insoluble agents can be delivered in soluble forms.

FIGS. 1 through 4 are illustrative of various devices that can be made according to the invention, and these devices are not to be construed as limiting, as the devices can take a wide variety of shapes, sizes and forms for delivering beneficial agents to the environments of use. For example, the devices can include buccal, implant, artificial gland, cervical, nasal, intrauterine, and blood delivery devices. The devices also can be sized, shaped, structured and adapted for delivering an active agent in streams, aquariums, fields, factories, reservoirs, laboratory facilities, hot houses, transportation means, naval means, hospitals, veterinary clinics, nursing homes, farms, zoos, sickrooms, chemical reactions, and the like.

DETAILED DESCRIPTION OF THE INVENTION

In accordance with the practice of the invention, it has now been found that osmotic delivery device 10 can be manufactured with a wall 12 formed of a material that does not adversely affect the agent, the buffer, and an animal host, and it is permeable to the passage of an external fluid, such as water and biological fluid, and it is substantially impermeable to the passage of drug, buffer, and the like. The selectively permeable materials comprising wall 12 are non-erodible and they are insoluble in fluids. Typical materials for forming wall 12 in one embodiment are cellulose ester and cellulose ether polymers having a degree of substitution, D.S. on the anhydroglucose unit from greater than 0 and up to 3 inclusive. By degree of substitution is meant the average number of hydroxyl groups originally present on the anhydroglucose unit comprising the cellulose polymer that are replaced by a substituting group. Representative materials include polymeric cellulose esters, cellulose ethers, and mixed cellulose esters and ethers, such as cellulose acylate, cellulose diacylate, cellulose triacylate, mono, di and tricellulose alkanoylates and aroylates. Exemplary polymers include cellulose acetate having a D.S. up to 1 and an acetyl content of up to 21%; cellulose diacetate having a D.S. of 1 to 2 and an acetyl content of 21 to 35%; cellulose triacetate having a D.S. of 2 to 3 and an acetyl content of 35 to 44.8%; cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioclanoate, and cellulose dipentate; and the like.

Additional semipermeable polymers include acetaldehyde dimethyl acetate, cellulose acetate ethyl carbamate, cellulose acetate phthalate, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; lightly cross-linked polystyrene derivatives; cross-linked poly(sodium styrene sulfonate), poly(vinylbenzyltrimethyl ammonium chloride), semipermeable polymers exhibiting a fluid permeability of $10^{-5}$ to $10^{-1}$ (cc.mil/cm$^2$.hr.atm) expressed as per atmosphere of hydrostatic or osmotic pressure difference across the semipermeable wall. The polymers are known to the art in U.S. Pat. Nos. 3,845,770; 3,916,899; and 4,160,020; and in Handbook of Common Polymers by Scott, J. R. and Roff, W. J., 1971, published by CRC Press, Cleveland, Ohio.

The expressions active agent, and beneficial agent, as used herein broadly include any compound that can be delivered from the device to produce a beneficial and useful result. The active agents include pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, sex sterilants, fertility inhibitors, fertility promoters, air purifiers, micro-organism attenuators, and other beneficial agents.

In the specification and the accompanying claims, the term agent includes drug, which latter term includes any physiologically or pharmacologically active substance that produces a local or a systemic effect(s) in animals, including warm-blooded mammals, humans, primates, household, sport, farm, zoo and laboratory animals, avians, reptiles and pisces. The term physiologically as used herein denotes the adminstration of a drug to produce normal levels and functions. The term pharmacologically denotes variations in response to the amount of drug administered to the host. Stedman's Medical Dictionary, 1966, published by Williams and Wilkins, Baltimore, MD. The active drugs that can be delivered include inorganic and organic drugs, without limitations, drugs that act on the central nervous system, depressants, hypnotics, sedatives, psychic energizers, tranquilizers, anticonvulsants, muscle relaxants, antiparkinson drugs, analgesics, anti-inflammatory drugs, anesthetics, muscle contractans, anti-microbials, anti-malarials, hormonal drugs, contraceptives, sympathomimetics, diuretics, anti-parasitics, neoplastics, hypoglycemics, ophthalmics, electrolytes, diagnostics, cardiovascular drugs, and the like.

Exemplary drugs that are poorly soluble, or insoluble in water and biological fluids that can be delivered by the invention include diphenidol, meclizine, prochlorperazine, thiethylperazine, anisindone, dizoxin, isofurophate, reserpine, acetazolamide, methazolamide, bendroflumethiazide, chlorpropamide, tolazamide, chlormadinone, allopurinol, methotrexate, acetyl sulfisoxazole, corticosteroids, hydrocortisone, triamcinolone, methyltisterone, and the like.

Exemplary drugs that are to soluble and can have their solubility modified in water and biological fluids for delivery by the invention include prochlorperazine edisylate, mecamylamine hydrochloride, procainamide hydrochloride, amphetamine sulfate, benzphetamine hydrochloride, phenmetrazine hydrochloride, bethanechol chloride, methacholine chloride, pilocarpine hydrochloride, atropine sulfate, methscopolamine bromide, isopropamide iodide, tridihexethyl chloride, phenformin hydrochloride, methylphenidate hydrochloride, and the like. Generally, the devices house from 0.05 mg to 5 grams, or more, with individual devices containing, for example, 0.25 mg, 1 mg, 5 mg, 25 mg, 250 mg, 500 mg, 1.5 g, and the like.

The term buffer as used herein denotes an acidic compound, a basic compound, a neutralizing agent, a compound that enters into a proton-transfer or neutralization reaction, or generically a compound that is capable in an aqueous solution of reacting with a counter basic agent, or a counter acidic agent, thereby producing an aqueous soluble agent salt within the device for dispensing the agent salt at a substantially zero order rate from the device over time. The salt produced in the compartment exhibits different thermodynamic properties than those imparted to the parent compound. During operation, the agent salt delivered from the device is continuously replaced by the presence of an equilibrium state generated in the device, which comprises the free agent, agent salt and excess buffer. Further in operation, the buffer continuously reacts with the free agent to continuously form a saturated solution of agent salt that is delivered from the device.

Exemplary acidic compounds that can be used for the purpose of the invention include the presently preferred solid acids such as fumaric acid, succinic acid, tartaric acid, citric acid, maleic acid, benzoic acid, ascorbic acid, oxalic acid, nicotinic acid, lactic acid, phthalic acids, pimaric acid, pimelic acid, tannic acid, urea hydrochloride, glycine, mandelic acid, glycolic acid, sodium monobasic phosphate, potassium bisulfite, potassium monobasic phosphate, and the like. The dissociation constant of representative acids in aqueous solution that can be used for selecting acids for use herein are disclosed in the Handbook of Chemistry, 39th Ed., pages 1644 to 1645, 1958.

Exemplary basic compounds that can be used for the purpose of the invention include urea, (sodium, potassium, calcium and magnesium salts of the acidic compounds such as sodium citrate, sodium maleate, sodium tartrate, potassium oxalate, and sodium potassium tartrate), sodium monophosphate, sodium biphosphate, sodium carbonate, sodium bicarbonate, sodium tetraborate, potassium aminobenzoate, potassium bicarbonate, potassium carbonate, potassium gluconate, sodium gluconate, potassium tribasic phosphate, dipotassium hydrogen phospahte, and the like.

Exemplary buffers that can be present in the compartment include aluminum ammonium sulfate, aluminum potassium sulfate, aluminum sodium sulfate, ammonium carbonate, ammonium phosphate, calcium gluconate, calcium lactate, magnesium oxide, potassium acid tartrate, dibasic ammonium phosphate, dibasic potassium phosphate, dibasic sodium phosphate, tribasic calcium phosphate, and the like. Typical buffers are disclosed in Food Chemical Codex, II, page 1012, 1972, Also, a Federal Drug Administration index of acceptable anions and cations this can be used for the present purpose, and a presentation of therapeutic salts is presented in J. Pharm. Sci., Vol. 66, pages 1 to 19, 1977.

Exemplary drug salts that can be formed in situ from a free drug and the appropriate acidic or basic compound include aminopromazine fumarate, caffeine sodium benzoate, cetiedil citrate, deserpidine oxalate, epinephrine bitartarate, ergotamine succinate, ergotamine tartarate, metoprolol tartarate, morphine phthalate pentahydrate, morpholine tartate, piperazine citrate, quinine lactate, reserpine citrate, theophylline sodium glycinate, theophylline potassium glycinate, thioproperazine fumarate, and the like.

The solubility of an agent, an acidic compound, a basic compound, or an agent salt in an external fluid that is imbibed into the device can be determined by various art known techniques. One technique consists in preparing a saturated solution comprising the external fluid plus the agent (or compound or salt) as ascertained by analyzing the amount of agent or the like present in a definite quantity of fluid. A simple apparatus for this purpose consists of a test tube of medium size fastened upright in a water bath maintained at constant temperature and pressure, for example, one atmosphere at 37° C., in which the fluid and agent or the like are placed and stirred by a motor driven rotating glass spiral. After a given period of stirring, a definite weight of the fluid is analyzed and the stirring continued for an additional period of time. If the analysis shows no increase of dissolved agent or the like after successive periods of stirring, in the presence of excess solid agent or the like in the fluid, the solution is considered to be saturated and the results are taken as the solubility of the agent or the like in the fluid. If the procedure indicates the agent or the like has limited solubility in the fluid, then other compounds can be used for preparing an agent salt with desired solubility for delivering the agent salt from the device.

The selection of a preferred acidic compound or a basic compound to react with a drug leading to an agent salt can be determined of techniques known to the art. One technique consists of adding the agent and its counter compound to fluid such that each solute is present in excess of that needed to form a mutually saturated solution. This mixture is stirred at constant temperature until mutually saturated solutions are formed. Next, a known volume of the solution is evaporated to dryness and the residual solid is weighed to indicate the total solubility of the agent salt in a given volume of fluid. Also, a second aliquot of solution is diluted with fluid and analyzed by an appropriate analytical technique such as ultraviolet or visible spectrophotometry, liquid or gas chromatography, or atomic absorption for determining the amount of agent present in the solution. The procedure is repeated using the same agent with a different counter compound for selecting a salt that has the desired solubility suitable for controlled delivery from the device.

The osmotic pressure of saturated solutions of various agent salts for delivery by the device can be measured in a commercially available osmometer that measures the vapor pressure difference between pure water and the solution to be analyzed, and according to standard thermodynamic principles, the vapor pressure ratio is converted into an osmotic pressure difference. An osmometer used for the present purpose is identified as Model 302 B, Vapor Pressure Osmometer, manufactured by the Hewlett Packard Co., Avondale, Pa. The rate of release of an agent salt from the device can be determined by using the procedures disclosed in U.S. Pat. Nos. 3,845,770; 3,916,899; and 4,160,020.

The expression passageway as used herein comprises means and methods suitable for releasing the agent from the device. The expression includes an aperture, orifice or bore through the wall formed by mechanical or laser procedures, or by eroding an erodible element such as a gelatin plug, in the environment of use. A detailed description of osmotic passageways and the maximum and the minimum dimensions for a passageway are disclosed in U.S. Pat. Nos. 3,845,770; 3,916,899, and 4,088,864.

The devices of the invention are manufactured by standard techniques. For example, in one embodiment the agent and other ingredients that may be housed in the compartment and an optional solvent are mixed into a solid, semi-solid or gel form by conventional methods such as ballmilling, calendering, stirring, or rollmilling, the solvent evaporated, and then pressed into a preselected shape. The wall forming the device can be applied by molding, spraying or dipping the pressed shape into wall forming materials. In another embodiment a wall can be cast into a film, shaped to the desired dimensions, sealed to define a hollow compartment that is filled with agent, and then closed with a passageway. The device also can be manufactured with an empty compartment that is filled through the passageway. High frequency electronic techniques can be used to provide devices with walls having clean edges. Another, and presently preferred technique that can be used is the air suspension procedure. This procedure consists in a suspending and tumbling the pressed agent and other indgredients in a current of air and the wall forming compositions until the wall is applied to the agent. The air suspension procedure is described in U.S. Pat. No. 2,799,241; in J. Am. Pharm. Assoc., Vol. 48, pages 451 to 459, 1959; and ibid, vol. 49, pages 82 to 84, 1960. Other standard manufacturing procedures are described in Modern Plastics Encyclopedia, Vol. 46, pages 62 to 70, 1969; and in Pharmaceutical Sciences, by Remington, 14th Ed., pages 1626 to 1678, 1970.

Exemplary solvents suitable for manufacturing the wall of the osmotic device include inert inorganic and organic solvents that do not adversely harm the wall, and the materials forming the final wall. The solvents broadly include a member selected from the group consisting of aqueous, alcohol, ketone, ester, ether, aliphatic, hydrocarbon, halogenated, cycloaliphatic, aromatic, heterocyclic solvents, and mixtures thereof. Typical solvents include acetone, diacetone, methanol, ethanol, isopropyl alcohol, butyl alcohol, methyl acetate, ethyl acetate, isopropyl acetate, n-butyl acetate, methyl isobutyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethyl bormamide, benzene, toluene, naphtha, 1,4-dioxane, tetrahydrofuran, diglyme, water and mixtures thereof such as acetone and water, acetone and methanol, acetone and ethyl alcohol, methylene chloride and methanol, and ethylene dichloride and methanol. Illustrative of mixed solvents are acetone-methanol (80:20), acetone-ethanol (90:10) methylene-dichloride-methanol (80:20), nitroethane-ethanol (50:50), nitroethane-ethanol (80:20), ethyl acetate-ethanol (80:20), ethylene dichloride-methanol (80:20), methylene dichloride-methanol (78:22), acetone-water (90:10), chloroform-methanol (80:20), methylene dichloride-ethanol (79:21), methylene chloride-methanol-water (75:22:3), carbontetrachloride-methanol (70:30), expressed as (weight:weight), and the like.

The following examples are merely illustrative of the present invention, and they should not be considered as limiting the scope of the invention in any way, as these examples and other equivalents thereof will become more apparent to those versed in the art in the light of the present disclosure, the drawings and the accompanying claims.

EXAMPLE 1

An osmotic therapeutic device for the controlled and continuous oral release of the beneficial drug theophylline was made as follows: first, 125 mg of theophylline, 520 mg of L-tartaric acid and 6 mg of poly(vinyl pyrrolidone) were blended to form a homogenous blend, and the composition fed into a tablet press and pressed at 5 to 6 tons pressure. Next, the pressed composition was coated with a semipermeable wall of cellulose acetate having an acetyl content of 32% using an air suspension coater. A 5% polymer solution in acetone-water, 90:10 wt-wt, was used for forming the semipermeable wall. A passageway having a diameter of 10 mils was laser drilled through the wall for delivering the drug from the device. Accompanying FIG. 5 depicts the cumulative percent of theophylline tartarate released by the device over time. The theophylline free base had a solubility of 10 mg/ml in water at 37° C. and the theophylline tartarate had a solubility of 220 mg/ml of water at 37° C.

EXAMPLES 2-9

The procedure of Example 1 is repeated with conditions as previously described except in the present examples the drug and the buffer in the device comprise metoprolol and fumaric acid, metoprolol and tartaric acid, indomethacin and sodium succinate, theophyhlline and sodium glycine, theophylline and sodium citrate, theophylline and sodium tartrate, and theophylline and citric acid.

The devices of this invention provide an unique means for dispensing of numerous agents. While there has been described and pointed out the novel features of the invention as applied to preferred embodiments, those skilled in the art will appreciate that various modifications, changes and omissions in the devices illustrated and described can be made without departing from the spirit of the invention.

We claim:
1. An oral, osmotic device for the controlled delivery of a beneficial drug comprising:

(a) a shaped wall formed of a member selected from the group consisting of cellulose acylate, cellulose diacylate, cellulose triacylate, and mixtures thereof, which wall is permeable to the passage of an external fluid and substantially impermeable to the passage of drug, the wall surrounding and forming:

(b) a compartment containing the beneficial drug selected from the group consisting of theophylline, theophylline sodium glycinate and theophylline potassium glycinate, and a buffer acid that is soluble in fluid imbibed into the compartment and provides an environment in the compartment of the osmotic device that aids in the delivery of the theophylline member from the osmotic device, the buffer acid a member selected from the group consisting of fumaric, succinic, maleic and lactic; and, (c) a passageway in the wall for delivering the theophylline member from the compartment at a controlled rate over a prolonged period of time.

2. The oral, osmotic device for the controlled delivery of the theophylline member according to claim 1, wherein the buffer acid interacts with the theophylline member and produces a buffer theophylline member that acts as its own osmotically effective solute for controlled delivery through the passageway from the osmotic device.

3. An oral, osmotic device for the controlled delivery of a beneficial drug, comprising:

(a) a shaped wall formed of a member selected from the group consisting of cellulose acylate, cellulose diacylate, cellulose triacylate, and mixtures thereof, said wall permeable to the passage of an external fluid and substantially impermeable to the passage of drug, which wall surrounds and forms;

(b) a compartment for containing a beneficial drug;

(c) the beneficial drug indomethacin in the compartment, and a buffer that is soluble in fluid imbibed into the compartment and provides an environment in the compartment that aids in the delivery of indomethacin from the osmotic device, the buffer a member selected from the group consisting of sodium glycinate, sodium citrate, sodium tartrate, sodium succinate and sodium maleate; and, (d) a passageway in the wall for delivering the indomethacin from the compartment at a controlled rate over a prolonged period of time.

4. The oral, osmotic device for the controlled delivery of indomethacin according to claim 3, wherein the buffer interacts with the indomethacin and produces a buffered indomethacin that acts as its own osmotically effective solute for controlled delivery through the passageway from the osmotic device.

* * * * *